United States Patent
Apelqvist et al.

(10) Patent No.: US 6,468,975 B1
(45) Date of Patent: Oct. 22, 2002

(54) LIVER SPECIFIC BILE ACID DERIVATIVES OF THE GLUCOCORTICOID ANTAGONIST RU486

(75) Inventors: Theresa Apelqvist, Huddinge (SE); Jinchang Wu, Huddinge (SE); Konrad Koehler, Huddinge (SE)

(73) Assignee: Karo Bio AB, Huddinge (SE)

( * ) Notice: Subject to any disclaimer, the term of this patent is extended or adjusted under 35 U.S.C. 154(b) by 0 days.

(21) Appl. No.: 09/937,374

(22) PCT Filed: Mar. 18, 2000

(86) PCT No.: PCT/EP00/02429

§ 371 (c)(1),
(2), (4) Date: Feb. 11, 2002

(87) PCT Pub. No.: WO00/58337

PCT Pub. Date: Oct. 5, 2000

(30) Foreign Application Priority Data

Mar. 27, 1999 (GB) ............................................... 9907048

(51) Int. Cl.[7] .............................. A61K 31/56; C07J 9/00; C07J 41/00
(52) U.S. Cl. .......................... 514/17; 514/169; 514/179; 552/549; 552/550
(58) Field of Search ................................. 552/550, 549; 514/179, 169, 170

(56) References Cited

U.S. PATENT DOCUMENTS

| 2,441,129 A | 5/1948 | Berezeller | 260/397.1 |
| 4,418,059 A | 11/1983 | Laalezari | 424/180 |

FOREIGN PATENT DOCUMENTS

| WO | WO 98/27986 | 12/1977 |
| WO | WO 99/63976 | 6/1999 |

OTHER PUBLICATIONS

"Liver–specific Drug Targeting by Coupling to Bile Acids", Kramer et al., *The Journal of Biological Chemistry*, Sep. 15, 1992, vol. 267, No. 26, pp. 18598–18604.

"RU–486 (Mifepristone) ameliorates diabetes but does not correct deficient β–adrenergic signalling in adipocytes from mature C57BL/6J–ob/ob mice", Gettys et al., *International Journal of Obesity* (1997), No. 21, pp. 865–873.

*Primary Examiner*—Barbara P. Badio
(74) *Attorney, Agent, or Firm*—Todd E. Garabedian; Wiggin & Dana LLP

(57) ABSTRACT

Novel glucocorticoid receptor ligands and methods of treating diseases such as diabetes, wherein the ligands have general formula (I)

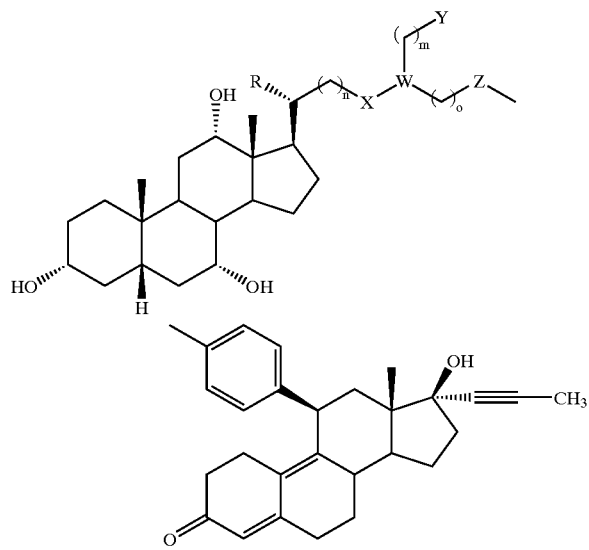

wherein the variables are as defined by the present specification.

10 Claims, No Drawings

LIVER SPECIFIC BILE ACID DERIVATIVES OF THE GLUCOCORTICOID ANTAGONIST RU486

This application is a 371 of PCT/EP00/02429 filed Mar. 18, 2000.

FIELD OF THE INVENTION

This invention relates to novel compounds that are liver selective glucocorticoid receptor antagonists, to methods of preparing such compounds, and to methods for using such compounds in the regulation of metabolism, especially lowering serum glucose levels.

BACKGROUND OF THE INVENTION

Glucocorticoid Receptor Antagonists

A major problem with both Type 2 and Type 1 diabetes is that there is excessive and inappropriate production of glucose by the liver. This abnormality is the primary cause of fasting hyperglycemia and occurs in addition to defects in regulation of insulin release and in peripheral sensitivity to insulin. Thus, agents that decrease liver glucose production would be beneficial for treating both Type 2 and also Type 1 diabetes.

Intensive treatment of the hyperglycemia of Type 1 diabetes mellitus has been shown to markedly decrease the development of ocular, renal and neuropathic complications, and there is evidence that intensive treatment is also beneficial for Type 2 diabetes. The available data also indicate that most patients are currently not receiving ideal and state-of-the-art treatment for either Type 2 or Type 1 diabetes. This inadequacy exists in spite of the availability of several different types of preparations of insulin for treatment of both Type 2 and Type 1 diabetes, and of a number of additional modalities, including agents that stimulate insulin release (e.g., sulfonylureas), influence liver glucose production (e.g., metformin), affect the sensitivity to insulin (e.g., troglitazone) and glucose absorption (e.g., a-glucosidase inhibitors). In spite of the availabilitn of several different orally active agents that lower blood glucose levels, many patients with Type 2 diabetes also require insulin for control of their blood sugar levels. Overall, insulin usage in Type 2 diabetes exceeds that for Type 1 diabetes, and there is general agreement that there is a need for additional oraily active agents to treat Type 2 diabetes.

The glucocorticoid secretions of the adrenal gland (dominantly cortisol in humans) were so-named because of their ability to regulate glucose metabolism. These steroids stimulate the production of glucose in the liver by promoting gluconeogenesis, which is the biosynthesis or new glucose (i.e. not glucose from glycogen). Thus, in glucocorticoid insufficiency there is a tendency to hypoglycemia, Wvith decreased liver glucose production. Further development of Addison's disease in the diabetic generally leads to lowered glucose levels. Conversely, glucocorticoid excess can Drovoke frank diabetes in individuals with latent diabetes mellitus, and generaily aggravates glycemic control in established diabetics. Similar influences have been observed in various animal models.

The increased glucose production in response to glucocorticoids is due to effects on a number of proteins. Important among these are effects on various transaminases that convert amino acids to glucose precursors, and induction of glucose-6 phosphatase and phosphoenolpyruvate carboxykinase (PEPCK). Even a modest increase of PEPCK, as obtained in transgenic mice, gives rise to hyperglycemia. In mice with Type 2 diabetes and increased levels of corticosterone (the endogenous glucocorticoid of that species) there is increased expression of PEPCK. This over expression of PEPCK can be repressed by treatment with the GR antagonist RU486 with a concomitant decrease in the hyperglycemia.

The considerations outlined above indicate that if actions of endogenous glucocorticoids on liver glucose production could be blocked in a specific manner, glycemic control could be improved for the benefit of the diabetic patients. However, to date, all means to block glucocorticoid action have been general. Thus, adrenalectomy leaves the patient with frank adrenal insufficiency and the problems of Addison's disease. Blockade of adrenal steroid production, for example by metyrapone, or of glucocorticoid action, for example with RU486 is ordinarily of limited duration of effectiveness and when it is effective also results in generalized adrenal insufficiency. Long term, compensatory ACTH hypersecretion and increased cortisol release that override the block generally overcome these treatments. By contrast, a liver-specific GR antagonist would not have these problems, should counter-act the increased liver glucose production in diabetes mellitus and should be useful for treatment of Type 2 diabetes.

A liver selective GR antagonist offers a number of advantages. First, it would decrease liver glucose production. This action will have a significant effect on glycemic control. In fact, excessive liver glucose production can be the major defect in Type 2 diabetes. Secondly, such a drug should enhance insulin sensitivity because of the overall improvement in the metabolic milieu and the amelioration of the hyperglycemia-induced defects in insulin action and secretion. The decreased demand on $\beta$-cell secretion, as a result of a reduction in glycemia, would retard the progressive $\beta$-cell dvsfunction characteristic of Type 2 diabetes. Another advantage of GR antagonist treatment compared with sulfonylurea or insulin treatment is that the patient would run a lower risk of hypoglycemia.

Previous efforts to block glucocorticoid action in diabetes have been hampered by the fact that any compounds used would generally block glucocorticoid action in all tissues and would lead to the potential problems of glucocorticoid insufficiency, such as hypotension, shock and uitimately death if the organism is exposed to sufficiently strong stress conditions. In contrast, a liver-selective GR-antagonist with minimal effects outside the liver could be used as a front line therapy for Type 2 diabetes, or could be used in conjunction with other existing therapies.

A strategy for obtaining liver selective compounds is to conjugate them with a bile acid such as cholate. This strategy has been recently reviewed by Kramer and Wess (Kramer, W.; Wess, G.; "Bile acid transport systems as pharmaceutical targets"; *Eur. J. Clin. Invest.* 1996, 26, 715–732). For example, bile acid conjugates have been prepared wvith the thyroid hormone T; and with HNIG-CoA reductase inhibitors. Both classes of conjugates were shown to reduce serum cholesterol levels while minimizing undesirable peripheral effects. These results demonstrate that bile acid conjugates are liver selective and are capable of delivering therapeutically useful concentrations of drug to the liver. An intriguing aspect of bile acid conjugates is that they are absorbed, excreted, and re-absorbed up to 12 times. Therefore bile acids represent an extremely efficient sustained release delivery mechanism.

While the bile acid conjugate strategy has previously been applied to several classes of drugs, it has not previously been applied to glucocorticoid ligands. For a glucocorticoid bile acid conjugate to be effective, it must maintain high affinity for both the glucocorticoid receptor and bile acid transporters and means to achieve this are non-obvious to those skilled in-the-art.

DESCRIPTION OF THE INVENTION

In accordance with the present invention, compounds are provided which are glucocorticoid ligands, and have the general formula I:

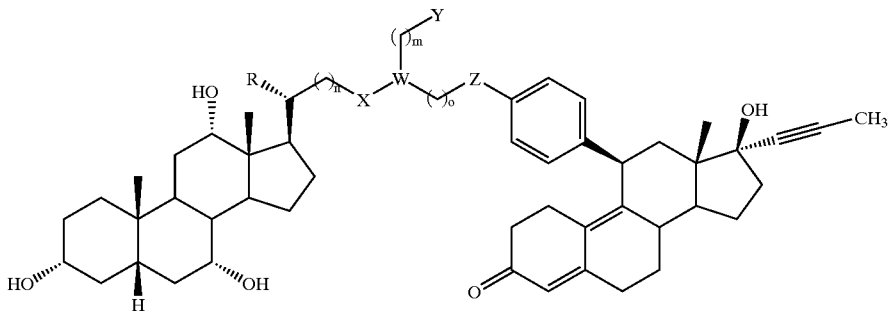

in which:
R is a hydrogen atom, an aliphatic hydrocarbon, an aromatic hydrocarbon, carboxylic acid or ester thereof, alkenyl carboxylic acid or ester thereof, hydroxy, halogen, or cyano halogen, or cyano, or a pharmaceutically acceptable salt thereof;

W is a methine carbon atom (CH) having the R, S, or racemic stereocheristrv;

X and Z are the same or are different and are a bond, an amide (—CONR'— or —NR'CO—), an amine (—NR'—), an ether (—O—), or a thioether (—S—) and R' is a hydrogen atom, an aliphatic hydrocarbon, or an aromatic hydrocarbon;

The subscripts n, o are the same or are different and are intergrers from one (1) to six (6), and mn in an integer from zero (0) to six (6);

Y is hydroxyl group, carboxylic acid or ester thereof, a tetrazole, an acylsulfonamide (—CONHSO$_2$R" or —SO$_2$NHCOR" where R" is an aliphatic or aromatic hydrocarbon), or a pharmaceutically acceptable salt thereof.

In addition, in accordance with the present invention, a method for preventing, inhibiting, or treating a disease associated with a metabolic dysfunction or which is dependent upon the expression of a glucocorticoid receptor regulated grene is provided, wherein a compound of formula I is administered in a therapeutically effective amount. The compound of formula I is preferably also liver selective. Examples of such diseases associated ivith metabolic dvsfunctions or are dependent upon the expression of a glucocorticoid receptor regzulatedi gene are set out hereinafter and include diabetes and inflammation.

DETAILED DESCRIPTION OF THE INVENTION

The following definitions apply, to the terms as used throughout this specifications, unless otherwise limited in specific instances.

The term "glucocorticoid receptor ligand" as used herein is intended to cover any moiety that binds to a glucocorticoid receptor. The ligand may act as an agonist, an antagonist, a partial agonist, or a partial antagonist.

The term "aliphatic hydrocarbon(s) as used herein refers to acyclic straight or branched chain groups which include alkyl, alkenyl, or aikynyl groups.

The term "aromatic" hydrocarbonfs) as used herein refers to groups including aryl groups as defined herein. The term "aryl" as employed herein alone or as part of another group refers to monocylcic and bicyclic aromatic groups containing 6 to 10 carbons in the ring portion (such as phenyl or napthyl including 1-naphthyl and 2-naphthyl) and may be optionally substituted through available carbon atoms with 1, 2, or 3 groups selected from hydrogen, halo, alkyl, haloalkyL alkoxy, haloalkoxy, alkenyl, trifluoromethyl, trifluoromethyioxy, alkynyl, hydroxy, nitro, or cyano.

Unless otherwise indicated, the term "lower alkenyl" or "alkenyl" as used herein by itself or as part of another group refers to straight or branched chain radicals of 2 to 12 carbons, preferably 2 to 5 carbons, in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, and the like.

Unless otherwise indicated, the term "lower aikvnyl" or "alkvnyl" as used herein by itself or as part of another group refers to straight or branched chain radicals of 2 to 12 carbons, preferably 2 to 8 carbons, in the normal chain, which include one triple bond in the normal chain, such as 2-propynyl, 3-butynyl, 2-butynyl, 4-pentyvnl, 3-pentynyl, 2-hexynyl, 3-hexynyl, 2-heptynyl, 3-heptynyl, 4-heptynyl, 3-octvnyl, 3-nonynyl, 4-decynyl, 3-undecynyl, 4-dodecynyl and the like.

The term "halogen" or "halo" as used herein alone or as part of another group refers to chlorine, bromine, fluorine, and iodine as well as CF3, with chlorine or bromine being preferred.

The term "amino" as emploved herein alone or as part of another group mav optionally be independently substituted with one or twvo substituents, which may be the same or different, such as alkyl, aryl, arvialkyl, hydroxyaryl, heteroaryl, heteroarvialkyl, cycioheteroalkyi, cycyoheteroaikylaikyi, cycloalkyl, cyclioalkylalkyl, haloalkyl, hydroxyalkyl, alkoxyalkyl or thioalkyl. These substituents may be further substituted with a carboxylic acid or any of the substituents for alkyl as set out above. In addition, the amino substituents may be taken together with the nitrogen atom to which the are attached to form 1-pyrrolidinyl. 1-piperidinyl. 1-azepinyl, 4-morpholinyl, 4-thiamorpholinyl, 1-piperazinvi, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

The compounds of formula I can be present as salts, in particular pharmaceutically acceptable salts. If the compounds of formula I have, for example, at least one basic center, they can form acid addition salts. These are formed, for example, Wvith strong inorganic acids, such as mineral acids, for example sulfuric acid, phosphoric acid or a hydrohalic acid, with strong organic carboxyiic acids, such as alkanecarboxyiic acids of 1 to 4 carbon atoms which are unsubstituted or substituted, for example, by halogen, for example acetic acid, such as saturated or unsaturated dicarboxylic acids, for example oxalic, malonic, succinic, maleic, fimaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$–$C_4$)-alkyl- or aryl-sulfonic acids which are unsubstituted or substituted, for example by halogen, for example methane- or p-toluene-sulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyipropylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

Preferred salts of the compounds of formula I which include a basic group include monohydrochloride, hydrogensulfate, methanesulfonate, phosphate or nitrate.

Preferred salts of the compounds of formula I which include an acid group include sodium, potassium and magnesium salts and pharmaceutically acceptable organic amines.

Preferred are compounds of the invention of formula I wherein R is a methyl group.

Preferred are compounds of the invention of formula I wherein Y is carboxylic acid (COOH), ester, or pharmaceutically acceptable salt thereof.

Preferred are compounds of the invention of formula I wherein X is an amide (—CONR').

Preferred are compounds of the invention of formula I wherein Z is an amide (—CONR"—).

Preferred are compounds of the invention of formula I wherein m is zero (0), n is two (2) and o is two (2).

Preferred compounds of the invention have the structures

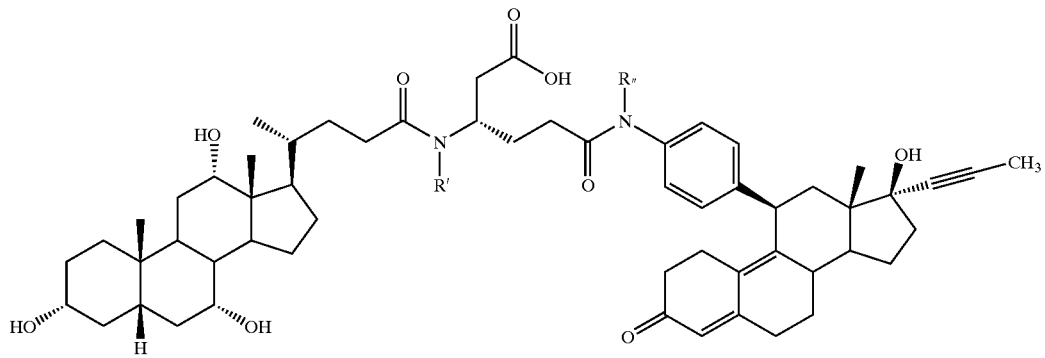

The compounds of formula I may be prepared by the exemplary processes described in the following reaction schemes. Exemplary reagents and procedures for these reactions appear hereinafter and in the working Examples.

Compounds of formula I of the invention can be prepared using the sequence of steps outlined in Scheme 1 to 2 set out below.

The compounds of the invention are glucocorticoid receptor antagonists or thyroid receptor agonists, that are preferably liver selective, and as such are useful in the treatment of diabetes (alone or in combination with agents that stimulate insulin release such as sulfonylureas, influence liver glucose production such as metformin, affect the sensitivity to insulin such as troglitazone, or inhibit glucose absorption such as α-glucosidase inhibitors).

The compounds of the invention can be administered orally or parenterally such as subcutaneously or intravenously, as well as by nasal application, rectally or sublingually to various mammalian species known to be subject to such maladies, e g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The active substance can be utilized in a composition such as tablet, capsule, solution or suspension or in other type carrier materials such as transdermal devices, iontophoretic devices, rectal suppositories, inhalant devices and the like. The composition or carrier will contain about 5 to about 500 mg per unit of dosage of a compound of formula I. They may be compounded in conventional matter with a physiologically acceptable vehicle or carrier, excipient, binder, preservative, stabilizer, flavor, etc., as called for by accepted pharmaceutical practice.

The following working Examples represent preferred embodiments of the present invention.

EXAMPLE 1

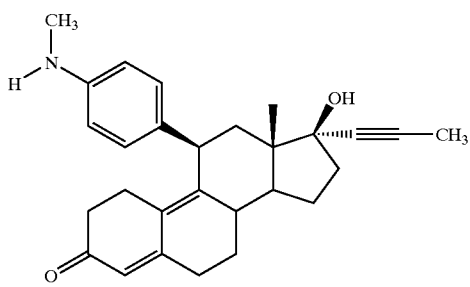

(a) 11β-(4-Methylaminophenyl)-17β-hydroxy-17α-(1-propynyl)estra-4,9-dien-3-one

A suspension of 11β-(4-dimethylaminophenyl)-17β-hydroxy-17α-(1-propynyl)estra-4,9-dien-3-one (0.94 g, 2.2 mmol), calcium oxide (1.23 g, 22.2 mmol) in methanol 12 ml) and DMF (12 mL) was cooled at 0° C. and a solution of iodine (1.67 g, 6.6 mmol) in DMF (4 mL) was slowly added. The mixture was stirred at the same temperature for one hour and was poured into ice-water. The precipitate was filtered, washed with water and purified by silica gel column (2% MyleOH/CH$_2$Cl$_2$) to give 0.9 g desired product. MS: (M+1)$^-$ 417.0; $^1$H-NMR (CDCl$_3$, δ, ppm): 0.53 (s, 3H, H-18); 1.87 (s, 3H, CH$_3$ of propynyl); 2.79 (s, 3H, N-CH$_3$); 4.33 (d, 1H, H-11); 5.74 (s, 1H, H-4); 6.51–7.00 (2xd, 4H, arom.).

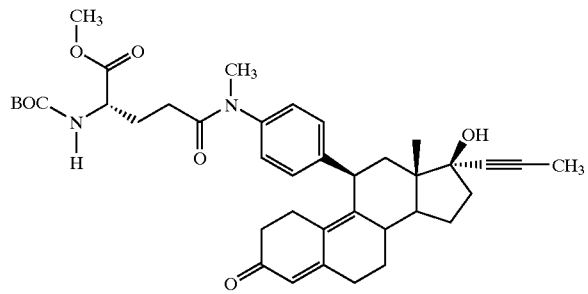

(b) 11β-{4-((4(S)-t-Butoxycarbonylamino-4(S)-methoxycarbonyl)butyryl-methyl-amino)phenyl}-17β-hydroxy-17α-(1-propynyl)estra-4,9-dien-3-one A solution of 11β-(4-methylaminophenyl)-17β-hydroxy-17α-(1-propynyl)estra-4,9-dien-3-one (0.9 g, 2.17 mmol), N-t-butoxycarbonyl methyl glutamate (0.63 g, 2.42 mmol) in DMF (10 mL) was cooled at 0° C. and diisopropyl ethylamine (0.83 mL, 4.8 mmol), O-(1H-benzotriazol-1-yl)-N,N,N',N'-tetramethyluronium tetrafluoro-borate (TBTU) (0.77 g, 2.42 mmol) were added subsequently. The reaction was allowed to reach room temperature and the stirring was continued for 2 days. The mixture was poured into ice-water with stirring. The precipitate was filtered and washed with water. The dried solid was purified by silica gel chromatography (2–5% MeOH/CH,Ck,) to give 0.93 g of the desired product. MS: (M+1)$^+$ 659.5. $^1$H-NMR (CDCl$_3$, δ, ppm): 0.46 (s, 3H, H-18); 1.38 (s, 9H, Boc); 1.85 (s, 3H, CH$_3$ of propynyl); 3.19 (s, 3H, N-CH$_3$); 3.68 (s, 3H, OCH$_3$); 4.08 (m, 1H, CH); 4.15 (d, 1H, H-11); 5.75 (s, 1H, H-4); 7.02–7.24 (2xd, 4H, arom.).

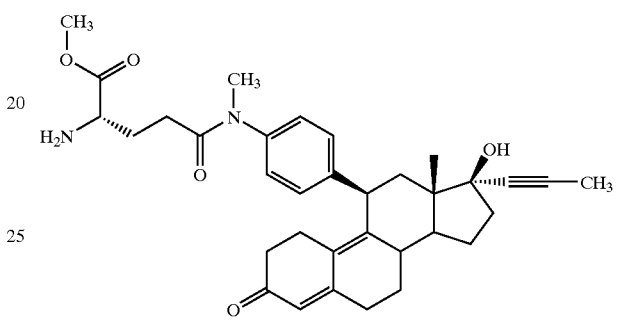

(c) 11β-{4-((4(S)-Amino-4(S)-methoxycarbonyl)butyryl-methylamino)phenyl}-17β-hydroxy-17α-(1-propynyl)estra-4,9-dien-3-one Hydrochloride 11β-{4-((4(S)-t-Bittoxyvcarbonyl-amino-4(S)-methoxycarbonyl)butyryl-methylamino)phenyl}-17β-hydroxy-17α-(1-prop-ynyl)estra-4,9-dien-3-one (0.92 g, 1.40 mmol) was treated with freshly prepared saturated HCl/AcOEt for one hour and no starting material left monitored by TLC. All volatile materials were removed under vacuum to give 0.75 g the desired product as a yellowish solid. MS: (M+1)$^+$ 559.3. $^1$H-NMR (CDCl$_3$, δ, ppm): 0.47 (s, 3H, H-18); 1.86 (s, 3H, CH$_3$ of propynyl); 3.21 (s, 3H, N-CH$_3$); 3.77 (s, 3H, OCH$_3$); 4.21(m, 1H, CH); 4.40 (m, 1H, H-11); 5.77 (s, 1H, H-4); 7.24 (m, 4H, arom.); 8.97 (b, 2H, NH$_2$).

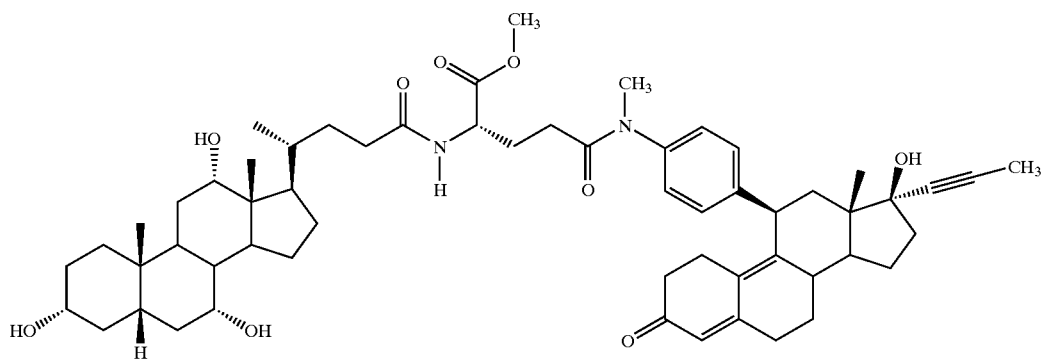

(d) 11β-{4-((4(S)-Cholic Amido-4(S)-methoxycarbonyl)butyryl-methylamino)-phenyl}-17β-hydroxy-17α-(1-propynyl)estra-4,9-dien-3-one A solution of 11β-{4((4(S)-amino-4(S)-methoxycarbonyl)butyryl-methylamino)phenyl}-17β-hydroxy-17α-(1-prop-ynyl)estra-4,9-dien-3-one hydrochloride (0.74 g, 1.24 mmol), cholic acid (0.65 g, 1.60 mmol) in DMF (10 mL) was cooled at 0° C. and diisopropyl ethyvamine (0.83 mL, 4.76 mmol), TBTU (0.51 g, 1.60 mmol) were added subsequently. The reaction was allowed to reach room temperature and the stirring was continued for two davs. The mixture was poured into ice water with stirring. The precipitate was filtered, washed with water and dried. The residue was purified by silica gel column (5–10% MeOH/CH$_2$Cl$_2$) to give 0.29 g product. MS: (M+1)$^+$ 949.6. $^1$H-NMR (CDCl$_3$, δ, ppm): (s, 3H, CH$_3$); 0.72 (s, 3H, CH$_3$); 0.89 (s, 3H, CH$_3$); 0.98 (d, 3H CH$_3$); 1.85 (s, 3H,CH$_3$ of propynyl); 3.20 (s, 3H, NCH$_3$); 3.45 (m, 1H); 3.65 (s, 3H, OCH$_3$); 3.74 (s, 1H); 3.95 (s, 1H); 4.4 (m, 2H); 5.75 (s, 1H, H-4); 6.80 (d, 1H, NH); 7.05–7.25 (2xd, 4H, arom.).

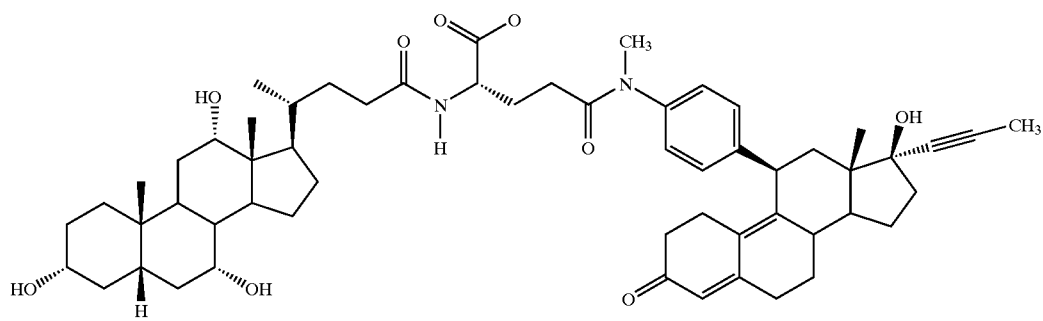

(e) 11β-{4-((4(S)-Cholic Amido-4(S)-carboxy)butyryl-methylamino)phenyl}-17β-hydroxy-17α-(1-propynyl)estra-4,9-dien-3-one 11β-{4-((4(S)-cholic amido-4(S)-methoxycarbonyl)butyryl-methylamino)phenyl-17β-hydroxy-17α-(1-propynyl)estra-4,9-dien-3-one (0.29 g, 0.3 mmol) was treated with lithium hydroxide (2M, 8 mL) and THF (8 mL) for two hours and no starting material left monitored by TLC. All volatile matters were evaporated and the residue was purified by silica gel column (10–15% MeOH/CH$_2$Cl$_2$, in the presence of 2% acetic acid) to give 0.23 g product. MS: (M+1)$^+$ 935.6. $^1$H-NMR (CDCl$_3$, δ, ppm): 0.49 (s, 3H, CH$_3$); 0.70 (s, 3H, CH$_3$); 0.92 (s, 3H, CH$_3$); 0.99 (d, 3H, CH$_3$); 1.86 (s, 3H, CH$_3$ of propynyl); 3.25 (s, 3H, NCH$_3$); 3.79 (s, 1H); 3.94 (s, 1H); 4.18 (d, 1H); 4.55 (d, 1H); 5.76 (s, 1H, H-4); 7.18–7.35 (2xd, 4H, arom.).

What is claimed:

1. A compound having the formula

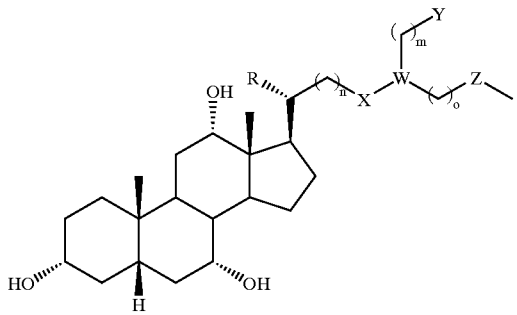

-continued

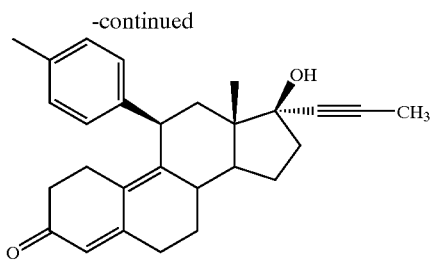

wherein

R is a hydrogen atom, an aliphatic hydrocarbon, an aromatic hydrocarbon, carboxylic acid or ester thereof, alkenyl carboxylic acid or ester thereof, hydroxy, halogen, or cyano halogen, or cyano, or a pharmaceutically acceptable salt thereof;

W is a methine carbon atom (CH) having the R, S, or racemic stereochemistry;

X and Z are the same or are different and are a bond, an amide (—CONR'— or —NR'CO—), an amine (—NR'—), an ether (—O—), or a thioether (—S—) and R' is a hydrogen atom, an aliphatic hydrocarbon, or an aromatic hydrocarbon;

the subscripts n, m, o are the same or different and are integers between zero (0) and six (6); and Y is hydroxyl group, carboxylic acid or ester thereof, a tetrazole, an acylsulfonamide (—CONHSO$_2$R" or —SO$_2$NHCOR" where R" is an aliphatic or aromatic hydrocarbon), or a pharmaceutically acceptable salt thereof.

2. The compound as defined in claim 1 wherein n is two (2).

3. The compound as defined in claim 1 wherein o is two (2).

4. The compound as defined in claim 1 wherein R is methyl (CH$_3$).

5. The compound as defined in claim 1 wherein X is a secondary amide (—CONH—).

6. The compound as defined in claim 1 wherein Y is a carboxylic acid, ester, or pharmaceutically acceptable salt thereof.

7. The compound as defined in claim 1 wherein Z is tertiary amide (—CONMe—).

8. The compound as defined in claim 1 which is 11β-{4-((4(S)-cholic amido-4(S)-carboxyl)butyryl-methylamino) phenyl}-17β-hydroxy-17α-(1-propynyl)estra-4,9-dien-3-one or a pharmaceutically acceptable salt thereof.

9. The compound as defined in claim 1 having the structure

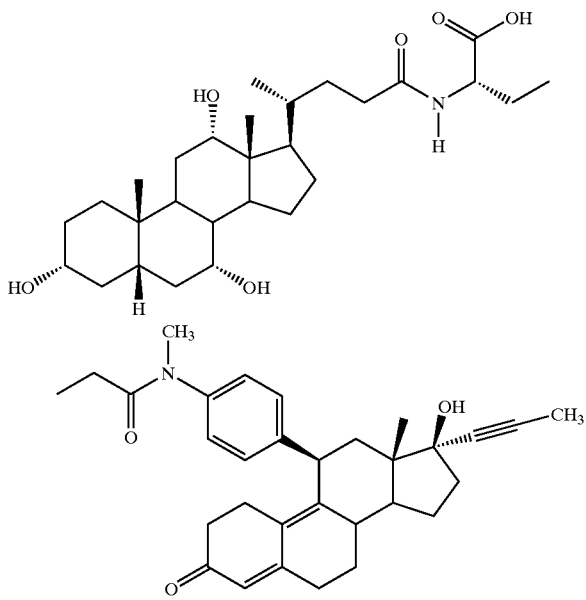

10. A method for treating diabetes comprising administering to a patient in need of treatment a therapeutically effective amount of the compound defined in claim 1.

* * * * *